(12) United States Patent
Heyman

(10) Patent No.: US 10,029,085 B1
(45) Date of Patent: Jul. 24, 2018

(54) TUBING ADJUSTABLE RETENTION TO BED CLOTHING

(71) Applicant: Arnold M. Heyman, Los Angeles, CA (US)

(72) Inventor: Arnold M. Heyman, Los Angeles, CA (US)

(73) Assignee: Neotech Products LLC, Valencia, CA (US)

( * ) Notice: Subject to any disclaimer, the term of this patent is extended or adjusted under 35 U.S.C. 154(b) by 13 days.

(21) Appl. No.: 14/756,452

(22) Filed: Sep. 4, 2015

(51) Int. Cl.
*A61M 39/08* (2006.01)
*F16L 3/16* (2006.01)
*F16L 3/137* (2006.01)

(52) U.S. Cl.
CPC ............ *A61M 39/08* (2013.01); *F16L 3/137* (2013.01); *F16L 3/16* (2013.01); *A61M 2039/087* (2013.01)

(58) Field of Classification Search
CPC ............ A61M 39/08; A61M 2039/087; A61M 5/1418; A61M 25/02; A61M 2025/026; A61M 2025/024; F16L 3/137; F16L 3/16; Y10T 24/1391; Y10T 24/2708; Y10T 24/31
See application file for complete search history.

(56) References Cited

U.S. PATENT DOCUMENTS

| | | | | |
|---|---|---|---|---|
| 580,293 A * | 4/1897 | Peterson | ............... | A41B 3/08 24/265 EC |
| 4,639,980 A * | 2/1987 | Peterson | ............... | A61M 25/02 128/DIG. 14 |
| 4,707,906 A * | 11/1987 | Posey | ............... | A61G 7/0503 128/DIG. 26 |
| 5,564,166 A * | 10/1996 | Roy | ............... | A45F 5/02 24/13 |
| 5,672,159 A * | 9/1997 | Warrick | ............... | A61M 16/0683 128/DIG. 26 |
| 5,709,665 A * | 1/1998 | Vergano | ............... | A61G 7/0503 128/DIG. 26 |
| 5,774,950 A * | 7/1998 | Stout | ............... | A61B 46/23 24/298 |
| 6,035,564 A * | 3/2000 | Cosmo | ............... | A44C 3/001 24/3.11 |
| 6,085,393 A * | 7/2000 | Tsui | ............... | A44B 99/00 24/3.12 |
| 6,247,211 B1 * | 6/2001 | Bell | ............... | A61M 25/02 24/298 |
| 6,301,751 B1 * | 10/2001 | Ohlson | ............... | A44C 3/001 24/3.11 |
| 6,419,660 B1 * | 7/2002 | Russo | ............... | A61M 25/02 128/DIG. 26 |

(Continued)

*Primary Examiner* — Robert Sandy
*Assistant Examiner* — Rowland Do
(74) *Attorney, Agent, or Firm* — Kelly & Kelley, LLP

(57) ABSTRACT

Apparatus for yieldably positioning bed-clothing relative to flexible fluid flow tubing, includes a holder for adjustable clipping to bed-clothing; a folding support for positioning tubing on bed-clothing; a rotatably adjustable connector between the holder and the folding support, the connector having surfaces that rub together during the adjustment to resist the rubbing, and provide limits to the rubbing and tubing displacement; and the folding support having a curved end facing the connector to resist the rotatable adjustment.

12 Claims, 2 Drawing Sheets

(56) References Cited

U.S. PATENT DOCUMENTS

| | | | | |
|---|---|---|---|---|
| 6,579,268 B1* | 6/2003 | Loining | ............... | A61M 25/02 |
| | | | | 604/174 |
| 6,776,137 B2* | 8/2004 | Kawai | ................. | F02D 9/1035 |
| | | | | 123/399 |
| 6,804,866 B2* | 10/2004 | Lemke | ............. | A61M 16/0683 |
| | | | | 24/3.11 |
| 7,284,729 B2* | 10/2007 | Walsh | ................. | A61M 25/02 |
| | | | | 128/877 |
| 7,284,730 B2* | 10/2007 | Walsh | ................. | A61M 25/02 |
| | | | | 128/877 |
| 8,607,366 B2* | 12/2013 | Austin | ............. | A41D 13/1236 |
| | | | | 2/300 |
| 8,974,401 B2* | 3/2015 | Taylor | ............... | A61M 25/002 |
| | | | | 600/585 |
| 2006/0020257 A1* | 1/2006 | Mambourg | .......... | A61M 39/08 |
| | | | | 606/1 |

* cited by examiner

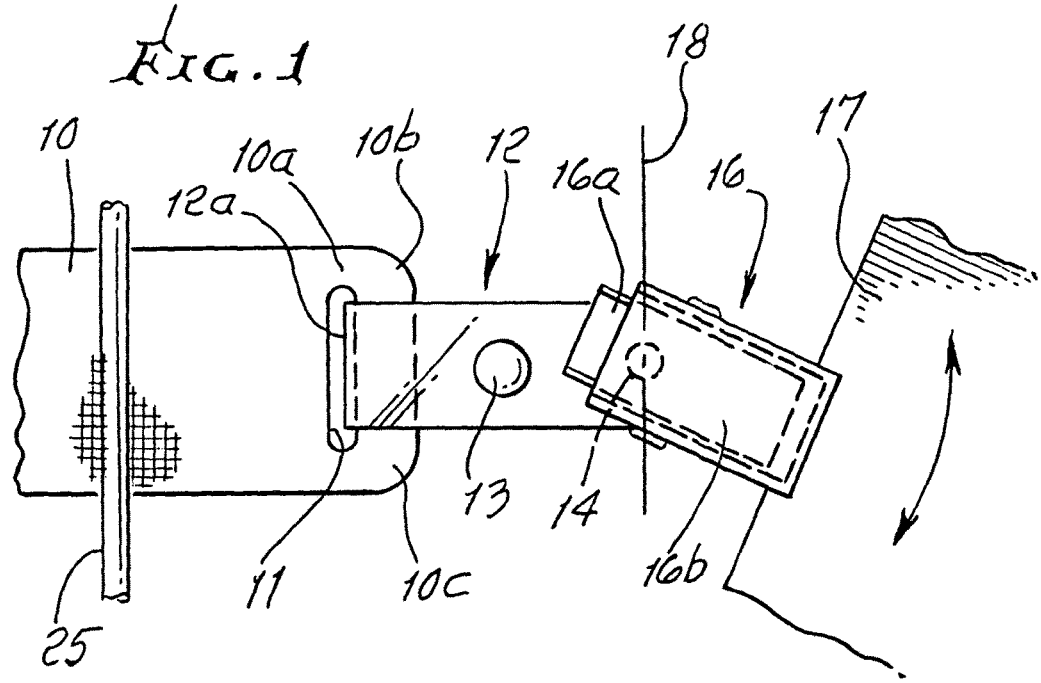
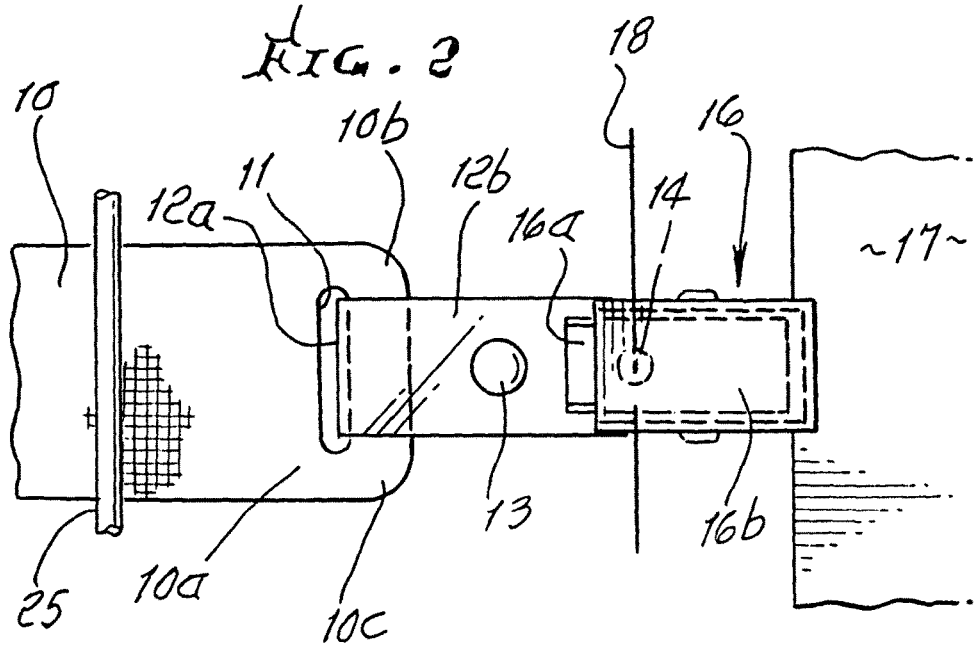

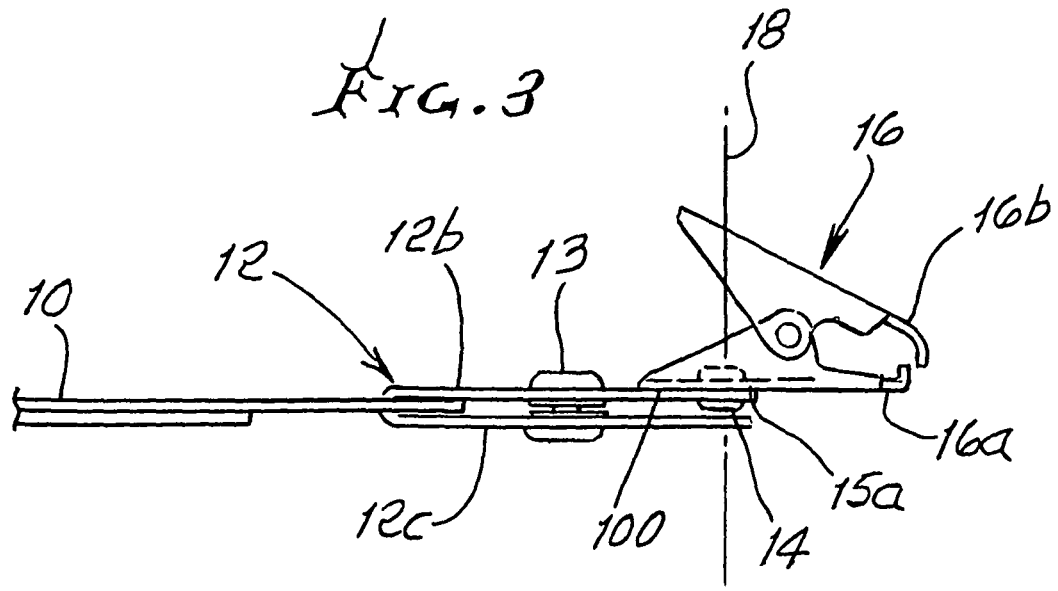
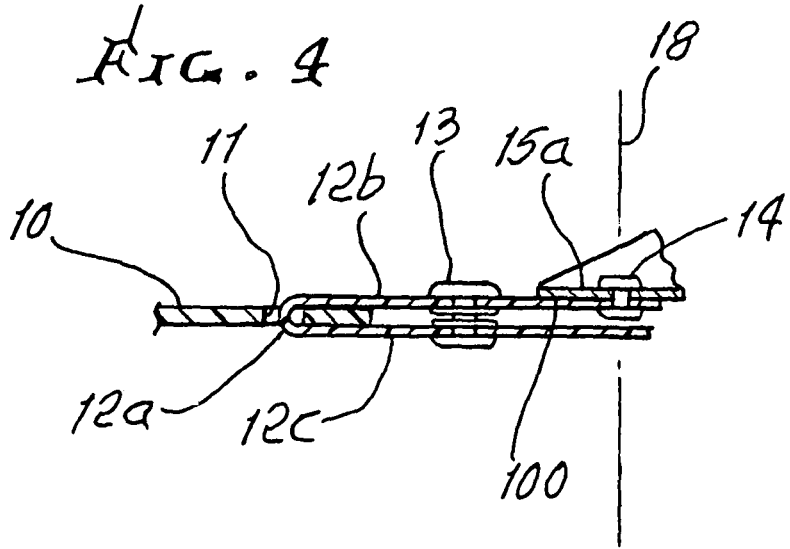

TUBING ADJUSTABLE RETENTION TO BED CLOTHING

BACKGROUND OF THE INVENTION

This invention relates generally to positioning of fluid flow treatment tubing related to a patient's supportive bed-clothing and more specifically concerns maintenance of positioning of such tubing during movement of the patient and such bed-clothing.

U.S. Pat. No. 4,308,642 describes apparatus for holding medically related conduits in a hospital setting. There is need for improvements to such devices, which minimize transmission of movement disturbances to such conduits, which could lead to conduit malfunctioning.

SUMMARY OF THE INVENTION

It is a major object of the invention to provide method and means for yieldably positioning flexible flow tubing relative to bed-clothing, to minimize flexing of the in-use tubing. As will be seen, the improved apparatus includes:
 a) a holder for adjustable clipping to bed-clothing,
 b) a folding support for positioning tubing on bed-clothing,
 c) a rotatably adjustable connector between the holder and the folding support, said connector having surfaces that rub together during rotatable adjustment to resist said rubbing, and provide limits to rotation of the connector relative to the holder by said rubbing,
 d) and said folding support having a curved end facing said connector to accommodate said rotatable adjustment.

Plastic material in face to face forcible contact during rotatable adjustment provides yieldable frictional adjustment, as during bed-clothing adjustment, with limits to rotation in opposite arcuate directions.

Another object includes providing a metallic pressure exerting holder exerting deforming pressure on said surfaces at a zone of relative rotation. Typically, the plastic material is in the form of a sheet folded to provide legs in surface to surface pressurized contact at said zone to yieldably resist said relative rotation. One of the plastic sheet legs extends protectively over the metallic holder, and intersects said axis of rotation. Accordingly, tubing near the apparatus is protected against folding, to a selected degree, by limited swiveling of the connector, as for example swiveling limits between 70° to 90°. This is further accommodated by providing a convexly curved edge of an elongated holder pad supporting the rotatable connection near said edge.

A further object is to provide a swivel connection providing frictional resistance to swiveling between arcuately spaced positions that limit swiveling.

These and other objects and advantages of the invention, as well as the details of an illustrative embodiment, will be more fully understood from the following specification and drawings, in which:

DRAWING DESCRIPTION

FIG. 1 shows an assembly in which the invention is provided;

FIG. 2 is a plan view of a pad to which medical tubing is attached, the pad being angularly adjustable on bed-clothing to re-position the tubing;

FIG. 3 is a plan view showing spaced positions of the pad and tubing, and an axis of adjustable swiveling of the pad, on bed-clothing; and FIG. 4 is a view of a folded plastic sheet having rubbing surfaces to hold the pad tubing in selected positions of angular adjustment (swiveling) relative to bed-clothing.

DETAILED DESCRIPTION

In the drawings, elongated pad 10 has an end portion 10*a* defining a widthwise extending through opening 11. The fold 12*a* of a plastic sheet 12 providing a folding support extends through opening 11, and legs 12*b* and 12*c* of plastic sheet 12 extend in the same direction toward and past rivet 13 interconnecting the folded legs. Leg 12*b* also has rotatable surface to surface connection including rotatable engagement at 100, by a rivet 14, to surface 15*a* of a jaw arm 16*a* of a clip or holder 16 whereby a rotatably adjustable connection is provided. The clip also has a second jaw arm 16*b*, and arms 16*a* and 16*b* are spring urged toward their positions as shown, whereby jaw arm ends may be urged toward one another to clip to bed-clothing 17. This enables swiveling of the pad and medical tubing 25 about axis 18 of rivet 14, to selectively and angularly re-position the bed-clothing 17, without disturbing the pad and tubing. Forcible sliding re-positioning of the surface of plastic leg 12*b* on and relative to the surface of the clip arm 16*a* enables forcible angular adjustment shifting about axis 18 of the bed-clothing relative to the pad and tubing, without disturbing said tubing. Flexible tubing 25 is typically adhesively attached to pad 10.

Note that the pad has convexly curved edge portions 10*b* and 10*c* spaced from the plastic sheet in all of its positions so as not to interfere the movement of the bed-clothing relative to the tubing. See FIG. 1. Rivet 13 positions the plastic legs for said swiveling.

The pad surface has selected identifying coloring.

The apparatus, accordingly, includes:
 a) a holder for adjustable clipping to bed-clothing,
 b) a folding support for positioning tubing on bed-clothing,
 c) a rotatably adjustable connector between the holder and the folding support, said connector having surfaces that rub together during said adjustment to resist said rubbing, and provide limits to said rubbing and tubing displacement,
 d) said folding support having a curved end facing said connector to resist said rotatable adjustment,
 e) said support having U-shape to define parallel legs, said connection located between one of said legs and said holder, there being a rivet interconnecting said legs at a location spaced from said connection.

The plastic material is in face to face forcible contact during said rotatable adjustment, with angular limits to said rotation.

The apparatus includes a metallic pressure exerting holder exerting deforming pressure on said surfaces at a zone of relative rotation.

The invention provides a hospital tubing positioned relative to hospital clothing, and including
 a) a holder connected to said hospital tubing and to hospital clothing,
 b) a rotatable sheet form connector connected to said holder, and said connector having a rotatable rubbing surface providing resistance to said rotation and means for limiting rotation of said surface relative to said tubing.

Also, the invention provides a swivel connection having pressure engaged surfaces providing frictional resistance to swiveling between angularly spaced positions that limit swiveling, and hospital tubing operatively connected to said swivel connection.

I claim:

1. An apparatus operable with bed-clothing and with flexible flow tubing for yieldably positioning said bed-clothing relative to flexible fluid flow tubing, comprising
 a) a holder (16) adjustably clipped to bed-clothing (17),
 b) an elongated pad (10) connected to a folding support connector (12), wherein the elongated pad (10) is adhesively attached to the tubing (25),
 c) a rotatably adjustable connector (14) between the holder (16) and the folding support connector (12), said holder (16) and support connector (12) having surfaces (100, 15a) that rotatably engage (rub together) during said clipping to bed clothing (17),
 d) said folding support connector (12) having a curved end (10b, 10c) to resist interference with the bed clothing (17),
 e) said support connector (12) having a U-shape defined by a fold (12a) between parallel legs (12b, 12c), wherein the fold (12a) in said support connector (12) extends through an opening (11) in said elongated pad (10), said rotatably engaging surfaces (100, 15a) being between one of said legs (12b) proximate the end of said one leg and said holder (16), there being a rivet (13) interconnecting said legs (12b, 12c) at a location spaced from said rotatably adjustable connector (14),
 f) said apparatus being elongated and overall substantially flat at the side of the holder (16) and including everywhere along the U-shaped support connector (12).

2. The apparatus of claim 1 including plastic material on said surface (100) in forcible contact with the surface (15a) on said holder (16) during said rotatable engagement.

3. The apparatus of claim 2 wherein the holder (16) is metallic and exerting deforming pressure on said surfaces (100, 15a) at a zone of relative rotation.

4. The apparatus of claim 3 wherein said plastic material is in the form of a sheet folded to provide said legs, one of which has a free end and is in surface contact with the holder at said zone to yieldably resist said rotation.

5. The apparatus of claim 4 wherein said holder defines an axis of rotation, and one of said plastic legs extends adjacent said metallic holder, and intersects said axis.

6. A hospital tubing (25) positioned relative to clothing (17), and including
 a) a holder (16) connected to said tubing (25) and to clothing (17),
 b) a rotatable sheet form connector (12) connected to said holder (16), and said connector (12) has a U-shape defined by a fold (12a) between two parallel legs (12b, 12c), wherein the fold (12a) in said connector (12) extends through an opening (11) in an elongated pad (10) that is configured for adhesive attachment of the hospital tubing (25), the holder (16) and one leg (12b) having a rotatable rubbing surface engagement (100) providing resistance to said rotation and allowing the holder (16) forcible rotation relative to the connector (12) extent proximate said clothing (17) and means for limiting rotation of said surface (100) relative to said tubing (25),
 c) said connector (12) being elongated and substantially flat at the side of the holder (16) and including everywhere along said one leg (12b) of said U-shaped connector (12).

7. The hospital tubing of claim 6 wherein said connector provides angular limits to said rotation.

8. The hospital tubing of claim 7 wherein said angular limits are between 70 degrees and 90 degrees.

9. The apparatus of claim 6 including plastic material on said surface (100) in forcible contact with the surface (15a) on said holder (16) during said rotatable engagement.

10. The apparatus of claim 9 wherein the holder (16) is metallic and exerting deforming pressure on said surfaces (100, 15a) at a zone of relative rotation.

11. The apparatus of claim 10 wherein said plastic material is in the form of a sheet folded to provide said legs, one of which has a free end and is in surface contact with the holder at said zone to yieldably resist said rotation.

12. The apparatus of claim 11 wherein said holder defines an axis of rotation, and one of said plastic legs extends adjacent said metallic holder, and intersects said axis.

\* \* \* \* \*